United States Patent [19]

Vadgama et al.

[11] Patent Number: 5,545,519
[45] Date of Patent: Aug. 13, 1996

[54] ELECTROLYTIC ANALYTICAL METHODS

[75] Inventors: Pankaj M. Vadgama; Mark F. Rosenberg, both of Manchester; Malcolm N. Jones, Sale, all of United Kingdom

[73] Assignee: Victoria University of Manchester, Manchester, England

[21] Appl. No.: 465,601

[22] Filed: Jun. 5, 1995

Related U.S. Application Data

[63] Continuation of Ser. No. 30,113, filed as PCT/GB91/01559, Sep. 12, 1991 published as WO92/05434, Apr. 2, 1992, abandoned.

[30] Foreign Application Priority Data

Sep. 13, 1990 [GB] United Kingdom ............ 9020046

[51] Int. Cl.⁶ ............ C12Q 1/00; G01N 33/92; C12N 9/00
[52] U.S. Cl. ............ 435/4; 435/14; 435/25; 435/26; 435/28; 435/183; 435/190; 435/192; 436/63; 436/71; 424/450
[58] Field of Search ............ 435/4, 14, 25, 435/26, 28, 183, 190, 192; 436/63, 71; 424/450

[56] References Cited

PUBLICATIONS

Kotowski et al, *Bioelectrochem. Bioenerg.*, vol. 19, No. 2, pp. 277–282, 1988.
Szoha et al, *Proc. Natl. Acad. Sci, USA*, vol. 75, No. 9, pp. 4194–4198, Sep. 1978.
Nakagawa, *Chemical Abstracts*, vol. 116, p. 416, Ref. #1696475, 1992 (JP-91,293,549, 12 Apr. 1990).
Rosenberg et al, *Biochem, Biophy. Acta*, vol. 115, pp. 157–165, 1992.
Mizutani et al, *Analytica Chemica Acta*, vol. 274, pp. 201–207, 1993.
Šnejdárková eta al, *Anal. Chem*, vol. 65, No. 6, pp. 665–668, Mar. 15, 1993.
Orbit Search Service, File Analytical Abstracts, Accession No. 52–04D00171, Anal. Lett., 22(5): Apr. 1989, Wu, T.–G. et al, "Potentiometric enzyme–amplified flow–injection analysis detectin system: behaviour of free and liposome–released peroxidase", pp. 1107–1124.

*Primary Examiner*—Elizabeth C. Weimar
*Assistant Examiner*—Abdel A. Mohamed
*Attorney, Agent, or Firm*—Cushman Darby & Cushman, LLP

[57] ABSTRACT

Enzyme electrodes having the enzyme enclosed within liposomes supported on, or in a membrane and immobilized therein are provided. The liposomes may be made using lipids and conveniently by "reverse phase evaporation". The enzyme electrodes incorporate conventional electrode elements, e.g., THE Clark electrode pair (Platinum/Silver) and additional membranes or screens, and used particularly in amperometric measurements. The enzyme can be an oxidase and is useful for measurement, directly or indirectly, of low molecular weight species generated by enzymic action, and effective for study of biological fluids.

15 Claims, No Drawings

ELECTROLYTIC ANALYTICAL METHODS

This is a continuation of application Ser. No. 08/030,113, filed as PCT/GB91/01559, Sep. 12, 1991, published as WO92/05434, Apr. 2, 1992 which was abandoned upon the filing hereof.

This invention relates to improvements in electrolytic analytical methods, and more particularly to improvements useful in electrolytic methods for determining hydrogen peroxide produced by the enzymatically catalysed oxidation of glucose at "enzyme electrodes." The invention is especially useful as an improved basis for the analysis of body fluids for glucose.

It is known to use electrolytic methods for detecting and measuring the concentration of glucose in liquids, and one of these is the so-called "enzyme electrode," in which an enzyme (glucose oxidase) is immobilised and used to promote the oxidation of the glucose in presence of oxygen so that the hydrogen peroxide thereby formed (as a co-product when the glucose is oxidised to gluconic acid) can then be measured amperometrically at an electrode, usually of platinum.

For use in a body fluid such as blood, there is the problem of interference from the many other components present, for example high molecular weight compounds and other oxidising or oxidisable compounds, and the environment is hostile towards the sensor. This can be overcome to some degree by screening the electrode with a membrane which is selectively permeable, and holds back the interfering components but still allows the hydrogen peroxide pass through. Cellulose acetate membranes have been proposed for this purpose.

However, difficulties have been in achieving a good proportional relationship between the glucose concentration and the electrode output signal over a sufficiently wide range, and the output current tends to reach a limit as the electrode effectively becomes "saturated" (usually at about only 5 mmol per liter concentration) and this severely limits the usefulness of the method as it does not allow sufficient flexibility and usefulness. This is especially relevant in clinical use as it is important to be able to measure concentrations up to 25 mmol per liter or even higher when dealing with diabetic patients suffering from hyperglycaemia (high concentrations of glucose in the blood).

There is, therefore, a need for an apparatus and method which allows the response to be made accurate and easily used (especially by becoming substantially linear) over a wider range of glucose concentrations. If effective enough over a sufficiently wide range, it can be more readily used for the monitoring and control of the condition and treatment of a patient, even in vivo.

We have now found that this problem can be overcome by modifying the electrode, so that the enzyme is not only immobilised but also is enclosed within liposomes.

The effect of this modification is that the range of glucose concentrations which can be satisfactorily measured is greatly extended and that the linearity of response (i.e. the response current at the electrode in relation to the concentration of glucose) is substantially linear over a far greater range. The mode of action is not clearly understood, but it is believed that the lipid serves to control the access of glucose to the enzyme without hindering the access of the oxygen needed for the action of the enzyme or the migration of the hydrogen peroxide produces during oxidation of the glucose towards the electrode at which it can be detected and measured.

This effect appears to be because the enzyme (e.g. glucose oxidase) encapsulated in liposomes can still act on any substrate which reaches it, but the lipid "wall" of the liposome provides (or acts as) a diffusion-limiting membrane. It also provides a biocompatible layer, which is of particular relevance and value when blood glucose is to be measured.

Thus according to our invention we provide improved enzyme electrodes in which the enzyme is enclosed within liposomes.

According to our invention we also provide an improved method for electro-analysis of solutions containing substances which utilise an enzyme, i.e. which interact with an enzyme, wherein the enzyme is enclosed within liposomes.

Especially, our invention relates to procedures in which one or more substrate compounds, by interaction with oxygen in the presence of an enzyme, generate hydrogen peroxide and this hydrogen peroxide is measured electrolytically. This measurement is most conveniently carried out in known manner, usually by amperometric methods. It is especially useful for the glucose oxidase/glucose system, but the invention may, however, also be used in relation to other enzyme systems if desired, for example alcohol oxidase systems, and other electrolytic techniques e.g. those employing potentiometric measurement of ion potentials.

The enzyme electrode, as suitable for use for determination of glucose, uses glucose oxidase entrapped in a large unilamellar liposome. The glucose diffuses in across the liposomal wall, thus generating hydrogen peroxide by enzymic catalysis, and this hydrogen peroxide is subsequently detected at the electrode surface.

We also provide enzyme-containing membranes, useful for incorporation in the improved electrodes of our invention and for use in the improved analytical methods of our invention, in which the enzyme is enclosed within liposomes.

Further, we also provide an electro-analytical cell incorporating an enzyme electrode, an enzyme-containing membrane or an enzyme-containing liposome as defined more fully herein.

Also, we provide, as new products useful for the production of electrodes and membranes of our invention, which comprise an enzyme enclosed within liposomes.

Liposomes are small vesicles (or particles or droplets) having an outer surface composed of a very thin layer of a lipid surrounding a volume of aqueous solution—which in the present invention contains the enzyme. Thus, they have a volume of an aqueous medium enclosed within a "wall" or "membrane" composed of lipid molecules. The lipid is usually a bipolar lipid, and especially a phospholipid. The lipid "wall" of the liposome then appears to serve to regulate the diffusion of the glucose into the interior aqueous zone without hindering the diffusion of the oxygen or hydrogen peroxide.

The liposomes may be made by intimate mixing of a lipid with an aqueous medium containing the enzyme. They usually form spontaneously when lipids are dispersed above their chain-melting temperatures, and the general procedure is known in the art. As a result of vigorous and thorough mixing of these components, the mixture can go through several stages, in which the lipid phase is spread and the components are progressively dispersed until eventually liposomes form and the phase changes result in the mixture becoming a suspension of the liposomes (each containing aqueous phase) suspended in more of the aqueous phase.

The lipid is preferably a bi-polar lipid (for example a phospholipid) so that its molecules congregate together in a bi-layer formation—two layers, each with their polar portions on the outside of the bi-layer and their non-polar portions together at the interior of the bi-layer. This bi-layer forms a "wall" which surrounds and encloses the aqueous medium containing the enzyme.

A variety of lipids (individually or as mixtures) may be used to form the liposomes, and an advantage of the invention is that the lipid may be chosen so that natural lipid materials may be used, which are in close relationship to materials found in natural cells and so are less liable to cause problems of bio-incompatibility.

The mixing and liposome formation may be assisted by the presence of an encapsulating aid, usually in the aqueous phase. In such cases, the ratio of the lipid to the encapsulating aid is in the range 5 to 20 parts of the lipid to each 1 part of the encapsulating aid.

The enzyme may be any enzyme which catalyses an oxidative process, especially one in which hydrogen peroxide is generated as a co-product. Such enzymes are commonly known as oxidases, or sometimes as dehydrogenases when their main function is to remove hydrogen from a substrate compound without necessarily forming hydrogen peroxide. The oxidases are preferred. This description is written mainly with reference to glucose oxidase, which is the most common and most useful enzyme of this type, and the invention is most applicable to systems using this enzyme. However, the invention is not necessarily restricted to this enzyme or to the measurement and detection of glucose alone, and other enzymes and appropriately matched substrates may be used, for example alcohol oxidase. Such enzymes are, in general, well known in the art and are usually soluble or readily dispersible in aqueous media.

The enclosing of the enzyme within the liposomes can be achieved by methods well known in the art for forming liposomes, using a lipid and an aqueous medium containing the enzyme. The method usually employs vigorous and thorough mixing of the lipid and the aqueous phase, optionally in the presence of an agent which facilitates the liposome formation. Such techniques are known in the art and include for example those known as "reverse phase evaporation." The ratio of the lipid to the liposome-forming aid ("encapsulating aid") may vary over a considerable range, depending on the components and conditions used, and may conveniently be determined by simple trial. Convenient proportions are in the range 5 to 20 parts of the lipid to each 1 part of the encapsulating aid, but larger or smaller proportions may be used if desired.

Examples of lipids include dimyristoylphosphatidylcholine, dipalmitoylphosphatidylcholine, distearoylphosphatidylcholine and mixtures thereof. Phosphatidyl inositol may also be included in the mixture used for forming the liposomes. The invention is not to be seen as limited to these lipids, as others may be used if so desired.

The size of the liposomes may vary, but may conveniently be in the range 25 to 1000 nm, and especially in the range 100 to 200 nm.

When knowledge of the permeability of the different liposomes is required, this can be determined conveniently by using liposomes with radio-labelled glucose—[$^{14}$C]glucose—trapped in them and measuring the extent to which this diffuses from the liposomes into surrounding aqueous media by following the radioactivity.

According to a further feature of the invention we provide enzyme electrodes wherein the liposomes, within which the enzyme is enclosed, are incorporated on or in a supporting carrier, especially on or in a membrane.

The liposomes may be be used by immobilising them upon a carrier, especially a membrane, so that they can be located in a convenient position and interposed between the main liquid being tested or analysed for oxidisable substrate compound (e.g. glucose) and the sensing electrode used for the measurement. The membrane on which they are thus immobilised may be for example a cellulose derivative, especially an ester of cellulose, for example cellulose acetate or cellulose nitrate (nitro-cellulose), though other natural or synthetic polymers may be used if desired, for example polycarbonate.

If the membrane material is sufficiently absorbent towards the liposomes, then they may be conveniently incorporated by contact, and such contact may be assisted by means, e.g. pressure, which can force the liposomes into it. For example, the differential pressure exerted by suction can be used to draw the aqueous suspension of liposomes into the membrane material so that the liposomes are deposited and held therein and the aqueous medium passes on. When the membrane material is not inherently sufficiently receptive to the liposomes, then the membrane material may be treated, physically and or chemically, to render it more receptive, for example by being rendered microporous so that the pores can trap the liposomes. If desired the liposomes, once in position on or in the membrane material, may be held more strongly in place by a treatment with a fixing agent which renders the liposomes less mobile but without destroying them or the enzyme in them. An example of such a treatment is the application of glutaraldehyde.

The amounts and proportions of the components of the liposomes may vary. A convenient proportion is in the range 0.1 to 0.5 mmol of the enzyme to each tool of lipid, but larger or smaller proportions may be used if desired.

We find further that the liposomes may be used at a variety of temperatures, but that they are especially effective at the phase transition temperature of the lipid. Surprisingly, at the phase transition temperature the state of the lipid appears to be exceptionally well suited to allowing more sensitive detection to be achieved.

It is therefore preferred to operate any cell or process using the membranes or liposomes of the present invention at a temperature close to the phase transition temperature of the lipid of the liposome, i.e. of the lipid which forms the enzyme-enclosing "skin" or "wall" of the liposomes. Thus, it is preferred that the operating temperature for use should be and especially within ±10 degrees C. of the phase transition temperature. It is convenient and useful to bear in mind that the activity of the enzyme itself can also vary with temperature, so it is desirable to match the optimum (or at least the satisfactory) working temperatures of the enzyme and the liposomes, so that the phase transition temperature of the lipid is reasonably close to that at which the enzyme has good activity. In the case of the liposomes made from a mixture of the two lipids dipalmitoylphosphatidylcholine ("DPPC") and phosphatidyl inositol ("PI"), this phase transition temperature is 35 degrees C.

This described use and effect of the liposome can also be used to measure the transition temperature of the lipid from which the liposome is derived, by means of an amperometric measurement using the enzyme/liposome component. This method can be carried out, for example, by measuring the current response in relation to the temperature while maintaining the glucose concentration constant and noting the maximum to which the current rises, which indicates the transition temperature. The procedure shows that the current response in relation to the temperature takes the form of a curve in which, when measurements are made at successive temperatures while maintaining the glucose concentration constant, the current rises with temperature to a maximum at the transition temperature and then falls thereafter—eventually reaching a minimum which then appears to be substantially independent of any further temperature rise.

The system for utilising the enzyme-containing liposomes may be varied in several ways, as can be seen by an expert in the art. Thus, for example, variations can be made in the concentration and amount of the entrapped enzyme and/or in the concentration or density of the liposomes on the support or carrier used (e.g. a membrane); both of these factors can increase the sensitivity of the enzyme electrode to the substrate on which the enzyme acts—e.g. glucose). Such variations may be used to optimise the system (i.e. the electrode and its performance) to suit particular circumstances or uses. The scope for optimisation can also include variations in the choice of the the combination of liposome components and the support or carrier material on which the liposome are used, as there can be some degree of inter-relation between these in use. The optimum form for any particular system or circumstances (e.g. the media in which the electrode is to be used) can then be found by simple trial.

The "active elements" of the electrode for use in this invention may be any known in the art, especially for amperometric analysis. Most conveniently it has a platinum anode, and a convenient form is the so-called Clark anode/cathode pair, which comprises a platinum anode surrounded by a silver cathode. For our invention, such an electrode pair can be used in an assembly comprising one or more membranes. These may be used to exclude blood cells and high molecular weight materials. Most suitably, two membranes are used—(a) one which is permeable to the hydrogen peroxide but not to components which could interfere with the measurements at the potentials used, and intended to provide major screening of the electrodes from the high molecular weight components of blood and possibly also from mechanical damage, and (b) another which which carries the immobilised enzyme as described more fully above. The number of membranes need not be limited to two, however, and as many may be used as is considered appropriate for the purposes of any specific electrode construction or use.

The preferred order in which these membranes are positioned, relative to the active electrode surfaces themselves (i.e. the anode and cathode), is for the screening membrane to be situated close to the electrodes and for the enzyme-bearing membrane to be situated beyond it, more remotely from the electrodes. This arrangement is not obligatory, however, and other dispositions of the membranes may be used of desired.

The membranes should also be secured in a sealed relationship to the electrodes, so that the liquids used cannot easily by-pass them. This is done very conveniently by making the body of the enzyme electrode or sensor assembly in the form of a container having two parts which fit together tightly in a manner which secures the membrane or membranes in place within it. Most conveniently, the parts of the body are secured together by one section being attached as a screw-on fit on to the other.

This assembly can be used by contacting it with the sample of blood or other liquid to be analysed, so that the solutions diffuse through the membranes and reach the electrodes. There, measurement (and most commonly amperometric measurement) can be carried out in conventional manner using conventional equipment. Measurements of the voltage applied and the current flows obtained can be recorded and/or presented in customary manner, for example on a chart recorder.

The process and membrane of the present invention may be used for a variety of purposes, but especially in connection with the measurement of glucose levels in blood and other body fluids, e.g. serum. They can, of course, also be used for measuring glucose contents of other liquids, including those which may not have such a highly hostile or demanding effect on electrodes and membranes (for example urine) and our invention is not restricted to their use for blood.

The present invention has the advantage that the measurement of the hydrogen peroxide (and hence of the glucose which gives rise to it) is greatly assisted. In particular, interference from proteins (e.g. fibrinogen) and other oxidisable compounds (e.g. ascorbic acid, uric acid and cysteine) commonly found in blood is substantially reduced to a level which allows the electrode linear range to be extended ten-fold (to about 30 per liter) and with conveniently speedy response times (of the order of 30–90 seconds). This enables the use of enzyme electrodes to be extended sufficiently for them to be applicable to measurement of unknown glucose concentrations for diabetic (especially hyperglycaemic) diabetic patients.

The facility offered by the invention to measure blood sugar levels easily and quickly, without having to determine first whether or not the sugar level is in the range which is reliably measurable and possibly having to dilute the sample if it is not, is a great advantage and lends itself to applications in which the link between the results of the blood sugar determination and the action to be taken in consequence of them (e.g. treatment or administration of drugs, especially insulin, to the patient) can be made more direct and immediate than formerly was practicable, even to the extent of automation.

They allow, for example, the determination of a patient's need for insulin on a "real time" basis instead of on the usual system of "standardised" dosages at pre-determined times which do not allow for any unpredicted change of behaviour pattern which could alter the patient's need for insulin. It also allows for the dosing to be administered at a continuing rate and continually adjusted, even automatically.

The invention is illustrated but not limited by the following Examples.

EXAMPLE 1

Liposomes were made by a reverse phase evaporation technique from 9 parts of dipahnitoylphosphatidylcholine ("DPPC") and 1 part of phosphatidyl inositol ("PI"), and an aqueous solution of the enzyme glucose oxidase.

The liposomes were incorporated into a membrane by absorption on to a filter composed of nitro-cellulose film, aided by suction to draw the liposomes into the nitro-cellulose.

An alternative procedure was to incorporate the liposomes into a microporous membrane or film of a polycarbonate polymer and then, when the liposomes had been deposited in its pores they were fixed there by treatment with glutaraldehyde.

The resulting membrane containing the liposomes was then fitted in a sealed manner over the electrode surfaces of a Clark electrode pair, consisting of a platinum anode surrounded by a silver cathode. This assembly was then covered by a further membrane consisting of a film of cellulose acetate. The whole assembly was then dipped into an aqueous solution of glucose, and a polarising voltage was applied across the electrodes. The platinum anode was thus made positive to the extent customary for amperometric measurements, for example to approximately 650 millivolts. The apparatus was connected to a recorder which measured and recorded the current flowing.

The glucose diffuses across the liposomal wall, thus generating hydrogen peroxide by enzyme catalysis. The hydrogen peroxide subsequently migrates to the platinum electrode surface and is detected and measured there.

The results observed showed that the range over which the relationship between response current and the glucose concentration was extended ten-fold compared with conventional electrode systems (up to 30 mmol per liter or more) by the use of the liposome-trapped enzyme. Response times were 30–90 seconds. This is practical for measurement of unknown glucose concentrations in the wide range required for diabetic patients.

The response (current flow) was also substantially linear over a similar range of glucose concentrations at temperatures between 29 and 46 degrees C., but was best at 35 degrees C. (the phase transition temperature of the lipid). The response current was also measured over a range of temperatures for the same concentration of glucose (15 mmol per liter) and was found to rise to a maximum of approximately 8.7 nA at 29 degrees C. to a maximum of almost 9.5 nA at 35 degrees C. (the phase transition temperature of the lipid), and then fall off steadily to 7.5 nA at 42 degrees C. and then remain substantially constant as the temperature was increased further.

This compares the sensor performance above and below the phase transition temperature of the particular lipid from which the liposomes were derived (35 degrees C.) and shows that the highest current response was obtained at the transition temperature.

EXAMPLE 2

LIPOSOME (REVERSE-PHASE EVAPORATION VESICLES, "REV") PREPARATION

Liposomes were prepared by a modification of the method described by F. Szoka and D. Papadjopoulos [1978, Proc. Natl. Acad. Sci. 75, 4194–4198] and were used primarily because of their large encapsulated volume for entrapping glucose oxidase. A proportion of tritium-labelled lipid was included for purposes of allowing the assay of the material, and this would not be required for use of the resulting liposomes in an enzyme electrode and so, for practical purposes, can then be omitted.

The lipid, DMPC (9 mg), was added to PI (1 mg) and 100 µl of [$^3$H] DPPC (2 µCi/ml) in 3 ml of distilled chloroform/methanol mixture (4:1). The purity of the lipids was checked by thin-layer chromatography on silica gel plates and the solvents were distilled in order to remove any traces of peroxides. The mixture was rotary evaporated at 60 degrees C. to yield a thin lipid film. This was then re-dispersed in 6 ml of 4:1 chloroform/methanol and 3 ml of nitrogen-saturated 1/10 phosphate buffered saline ("PBS," I=0.15 mol/l) containing 10 mg of glucose oxidase. The mixture was vortexed, followed by 4 minutes sonication in a bath-type sonicator (Decon FS 100, Decon Ultrasonics Ltd., Sussex, England) under nitrogen. The temperature of the bath was maintained at 30 degrees C. (i.e. above the phase transition temperature of the lipid). The resulting homogeneous emulsion was rotary evaporated at a temperature above the phase transition temperature of the lipid. After a viscous gel phase, gel inversion occurred with the formation of an aqueous suspension. This was purged with nitrogen for a further 15 minutes at a temperature above the phase transition temperature of the lipid to remove traces of organic solvent and to anneal any defects in the liposomes.

The above procedure was repeated using DPPC instead of the DMPC, and the temperature of the bath was maintained at 50 degrees C., and also using DSPC instead of the DMPC, and the temperature of the bath was maintained at 60 degrees C., i.e. above the phase transition temperature of the respective lipids).

To separate the encapsulated glucose oxidase from the non-encapsulated enzyme, the preparation was passed through a column of Sepharose 4B (30×1.5 cm) and eluted using PBS, pH 7.3, at a flow rate of 0.2 ml/min and fractions of 2 cm$^3$ were collected using an LKB Redirac Fraction Collector (Bromma, Sweden). Prior to the application of the liposome suspension, the column was pre-treated with a liposome dispersion to prevent adsorption of the liposomes on to the gel matrix [C. H. Huang, 1969, Biochemistry 8, 1344–352].

IMMOBILISATION OF THE LIPOSOMES ON A MEMBRANE

The liposomes were immobilised by filtering a predetermined volume (1 ml) of the suspension under vacuum on to a Millipore nitro-cellulose membrane (1 cm$^2$) of 0.45 µm pore size (Millipore Ltd., The Boulevard, Watford, Hertfordshire, England) followed by washing of the membrane with PBS buffer at pH 7.3.

The radioactivity of the Millipore membranes was determined by scintillation counting, by adding 4 ml of scintillation fluid to the membranes and counts were then used to assess the liposome density on each membrane. By relating the DPM for the membrane to the DPM/mole of lipid, the number of moles of the lipid on the membrane could be calculated and, since the number of moles of protein per mole of lipid was known, the number of moles of bound protein could also be ascertained. This was undertaken after the glucose responses of the appropriate membrane had been tested.

EXPERIMENTAL

A basic Clark oxygen electrode system (Rank Brothers, Bottisham, Cambridge, England) was used. The electrode was polarised at +650 mV for hydrogen peroxide detection, and the meter was linked to a chart recorder. The electrode consisted of a central 2-mm diameter platinum working electrode with an outer 12-mm diameter silver ring as the pseudoreference.

PROCEDURE FOR GLUCOSE DETERMINATION

An isotonic PBS buffer was used with aqueous samples. The surface of the hydrogen peroxide sensor was moistened with buffer solution to allow electrical contact between the working and pseudoreference electrodes. The appropriate Millipore membrane carrying immobilised enzyme-containing liposomes was then positioned over the electrode and was held in place by the screw-fit top of the electrode body.

Aliquots of a stock solution of 1M D-glucose solution were added to an appropriate volume of buffer in the sample chamber and the medium stirred until it was homogeneous. The steady state currents were then recorded. This procedure was repeated for a range of liposome membranes (DMPC/

PI, DLPC/PI and DSPC/PI), all of weight ratio 9:1. In addition, the glucose responses were measured over a range of temperatures using a thermostatted reaction cell. No hysteresis effects of the electrode response were observed on heating or cooling.

To ensure that the evaluations were reliable, control measurements were carried out using the same enzyme carried on the surface of a Millipore membrane but not in liposomal form, and the glucose responses were evaluated over a similar range of temperatures and in a similar manner, using comparable enzyme concentrations, as for the liposomal membranes.

A comparison was made of sensor performance both above and below the phase transition temperature of the constituent liposomal lipid molecules of dipalmitoylphosphatidylcholine. Increased glucose signals correlating with an increased permeability of the bi-layer lipid membrane were recorded above 42 degrees C.

The electrode response was found to embrace the required range of glucose concentrations and moreover, using liposomes prepared from different lipids, the electrode response was shown to depend upon the bi-layer permeabilities in relation to the lipid phase transition temperatures and as a consequence the linear ranges were duly altered.

The results demonstrate that enzyme encapsulation or immobilisation within liposomes extends the linear range of the electrode response and that the enzyme activity is partly dictated by the liposomal bi-layer's permeability. This ability to control the enzyme affinity for the substrate and to extend its useful range to higher glucose concentrations by using less permeable liposomes has considerable value for uses in which the monitoring of high glucose levels is required, for example in diabetic monitoring and in fermentation procedures.

VESICLE SIZE DISTRIBUTION ANALYSIS BY PHOTON CORRELATION SPECTROSCOPY (PCS)

The size of the vesicles was determined by a dynamic light-scattering technique using a Malvern Autosizer (Model No. 66143, Malvern Instruments, Malvern, England). This determined the hydrodynamic diameter on the basis of fluctuations in the scattered light intensity with time. The Autosizer gives the equivalent normal weight distribution of particle diameters, from which the weight-average diameter ($\bar{d}_w$) of the liposomes is obtained. Checks of the accuracy of the $\bar{d}_w$ values were made by using monodisperse latex beads with nominal diameters of 50 nm, 150 nm, and 244 nm. Measurements were made on liposomes dispersed in PBS (pH 7.3).

The liposomes prepared from different lipids have different permeabilities, and this effect can be used so that their permeability can be controlled and selected by an appropriate choice of the lipid component. For example, when liposomes made using the three compounds dimyristoyl, dipalmitoyl and distearoyl phosphatidyl choline as the lipid, the first of these three (the dimyristoyl derivative) is found to be the most permeable to glucose and the last (the distearoyl derivative) to be the least permeable to glucose. This was attributed to the differences in the phase transition properties of the lipids. Further, this effect of the lipid on the properties of the liposome for purposes of an enzyme electrode was found to affect the linear range of the electrode response—the liposomes derived from the least permeable lipids (of the three mentioned above, the distearoyl derivative) were found to have the largest linear range (at least 50 mM) with the most permeable liposomes (of the three mentioned above, the dimyristoyl derivative) having the smaller linear range (10 mM). In this way, the invention provides a means by which the linear range can be "controlled" by varying the nature of the lipid used. Also, it allows enzyme electrodes to be made in a form which can be used easily where relatively 35 high glucose levels need to be measured, for example in fermentation vessels.

For liposomes made from the three lipids mentioned above (dimyristoyl, dipalmitoyl and distearoyl phosphatidyl choline), there was a marked increase in glucose permeability at the phase transition temperature of the respective lipid, indicated by a marked increase in the electrode response.

ASSAY PROCEDURES

Fractions (2 ml) from gel chromatography were assayed for protein according to the procedure described by Lowry et al., (J. Biol. Chem. 193, 265–275.) using a glucose oxidase standard (0–20 µg/100 µl). In order to disperse the liposomal glucose oxidase, 100 ul SDS 1% (w/v) was added to each liposomal fraction and protein standards. SDS at this concentration has been shown not to inhibit or denature glucose oxidase in neutral media. The fraction were assayed for lipid by the [$^3$H] DPPC counts obtained by scintillation counting (Beckman LS 9800 USA). These parameters were then used to express the encapsulated glucose oxidase concentration in ug glucose oxidase/u mol lipid. The [$^3$H] DPPC (specific radioactivity 80Ci/mmol, code TRK 673) was purchased from Amersham International PLC, Amersham, Buckinghamshire, England, and the scintillation fluid used was Ecosinct A, supplied by National Diagnostics, Manville, N.J., USA.

In the above description, the following abbreviations are used, and the products as used in the work were obtained from The Sigma Chemical Company, Poole, Dorset, England:

"DPPC" is dipalmitoylphosphatidylcholine; (L-alpha-dipalmitoylphosphatidylcholine, product No. P-0763)

"DMPC" is dimyristoylphosphatidyl choline; (L-alpha-dimyristylphosphatidylcholine, product No. P-0888)

"DSPC" is distearoylphosphatidyl choline; (L-alpha-stearoylphosphatidylcholine, product No. P-1138)

"PI" is phosphatidyl inositol. (grade 1. product No. P-976).

We claim:

1. Enzyme electrodes, having at least one active electrode component appropriate for the performance of an electrolytic measuring function, in association with an enzyme, wherein the enzyme is enclosed within liposomes and the liposomes, within which the enzyme is enclosed, are incorporated on or in a supporting carrier.

2. Enzyme electrodes as claimed in claim 1 wherein the supporting carrier is a membrane.

3. Enzyme electrodes as claimed in claim 1 or claim 2 wherein the liposomes comprise a bi-polar lipid exterior enclosing the enzyme.

4. Enzyme electrodes as claimed in claim 3 wherein the bi-polar lipid is a phospholipid.

5. Enzyme electrodes as claimed in claim 4 wherein the lipid is phosphatidyl inositol, dimyristoylphosphatidylcholine, dipalmitoyl-phosphatidylcholine or distearoyl-phosphatidylcholine.

6. Enzyme electrodes as claimed in claim 1 or claim 2 wherein the size of the liposomes is in the range of 25 to 1000 nm.

7. Enzyme electrodes as claimed in claim 6 wherein the size of the liposomes is in the range of 100 to 200 nm.

8. Enzyme electrodes as claimed in claim 1 or claim 2 wherein the enzyme is an enzyme which catalyses an oxidative process in which hydrogen peroxide is generated as a co-product.

9. Enzyme electrodes as claimed in claim 8 wherein the enzyme is glucose oxidase.

10. Enzyme electrodes as claimed in claim 1 or claim 2 wherein the supporting carrier on which the liposomes are immobilized comprises a polycarbonate or a cellulose derivative.

11. Enzyme electrodes as claimed in claim 10 wherein the cellulose derivative is an ester of cellulose.

12. Enzyme electrodes as claimed in claim 11 wherein the ester of cellulose is a cellulose acetate or a cellulose nitrate.

13. In a method for electro-analysis of solutions containing substances which interact with an enzyme in an enzyme electrode, the improvement which comprises enclosing the enzyme within liposomes.

14. A method according to claim 13 wherein the liposomes in which the enzyme is enclosed are incorporated on or in a supporting carrier.

15. A method according to claim 14 wherein the carrier is a membrane.

* * * * *